United States Patent [19]

Curran et al.

[11] Patent Number: 4,914,091

[45] Date of Patent: Apr. 3, 1990

[54] ESTERS OF CEPHALOSPORIN DERIVITIVES

[75] Inventors: William V. Curran, Pearl River; Adma S. Ross, Suffern, both of N.Y.

[73] Assignee: American Cyanamid Company, Stamford, Conn.

[21] Appl. No.: 595,844

[22] Filed: Apr. 2, 1984

[51] Int. Cl.[4] .................. A61K 31/545; C07D 501/20
[52] U.S. Cl. .................................. 514/206; 544/227
[58] Field of Search ............... 544/22, 27; 514/202, 514/206

[56] References Cited

U.S. PATENT DOCUMENTS

| | | | |
|---|---|---|---|
| 3,935,204 | 1/1976 | Dahlén et al. | 544/27 |
| 4,755,598 | 7/1988 | Takanohashi | 540/227 |
| 4,797,395 | 1/1989 | Miyake | 540/227 |

OTHER PUBLICATIONS

Nakao et al., "Methoxycephalosporin compounds...," *Chem. Abst.* 92:146752t.

*Primary Examiner*—Donald G. Daus
*Attorney, Agent, or Firm*—Thomas S. Szatkowski

[57] ABSTRACT

Adamantane 1 carbonyloxymethyl 7β-[2-(2-aminothiazol-4-yl)-(Z)-2-methoxyiminoacetamido]-3-[(1,2,3-thiadiazol-5 yl)-thiomethyl]ceph-3-em-4 carboxylate is disclosed. It and other esters are used as orally administered anti bacterials".

3 Claims, No Drawings

1

ESTERS OF CEPHALOSPORIN DERIVITIVES

BACKGROUND OF THE INVENTION

Since the isolation of an active antibiotic from the mold *Cephalosporium acremonium* and the identification of the chemical structure of its nucleus, 7-aminocephalo-sporanic acid, a profusion of cephalosporins has been synthesized. Like penicillins, the cephalosporins owe their antibacterial activity to the presence of the β-lactam ring. Some cephalosporins exhibit a broad range of anti-bacterial activity, including activity against organisms, notably staphylococci, which are resistant to penicillins. Much of the broader range of activity shown by these cephalosporins over penicillins may be attributed to their resistance to a large number of β-lactamases which inactivate penicillins.

Both penicillins and cephalosporins may be administered parenterally. However, some penicillins, notably, phenoxy penicillin, indanyl carbenicillin, inter alia, may also be administered orally. However, by comparison, only a few cephalosporins may be administered orally. Moreover, despite considerable efforts directed toward finding side chains that will impart oral absorbability in cephalosporins, e.g., by analogy to penicillins, only D-(-)-arylglycyl- or dihydrophenylglycyl-substituted cephalosporins possess significant oral absorption. Chemistry and Biology of β-Lactam Antibiotics, 1: 391 (Robert B. Morin and Marvin Gorman, eds., 1982). Indeed, it has been opined that the synthesis of a cephalosporin with both broad spectrum antimicrobial activity and the capability of being orally absorbed will be fortuitous. Id. at 397.

The "prodrug" concept has been employed for both penicillins and cephalosporins; i.e., the administration of an inactive substance, such as an ester, which is metabolized by the body to an active component, e.g., the free acid. For penicillins, several esters have been synthesized which will be metabolized to active antibiotics. Among such esters are pivaloyloxymethyl, methoxymethyl and indanyl. However, the prodrug concept has not been as sucessful with cephalosporins. *Chemistry and Biology of β-Lactam Antibiotics*, 1: 404. Moreover, it is believed that with regard to cephalosporins in particular, whether an ester will render any given cephalosporin orally absorbable cannot be predicted. *Drugs of Today*, 19: 499–538 (1983). It has been opined that a general problem inherent with all cephalosporin esters may be the great propensity for these derivatives to give rise to a mixture of $\Delta^2$ and $\Delta^3$ isomers in vivo, the $\Delta^2$ isomers being inactive. Id. at 528.

In European Patent Application No. 81304416.1, the above-stated problems of obtaining an orally active, broad-spectrum cephalosporin are described. As noted therein, it has been difficult synthesizing a cephalosporin with a broad-spectrum of activity which (i) can be esterified to a prodrug and (ii) retains its activity upon metabolism. Specifically, such application discloses that certain 7-aminothiazole alkoxy-imino-acetamido cephalosporins either form orally inactive esters or esters with reduced spectrum of activity. In particular, the application discloses that such cephalosporins having at the 3-position a thiadiazolyl-thiomethyl have not been shown to form esters effective as prodrugs.

DESCRIPTION OF THE INVENTION

This invention relates to new cephalosporin esters which may be represented by the following formulas:

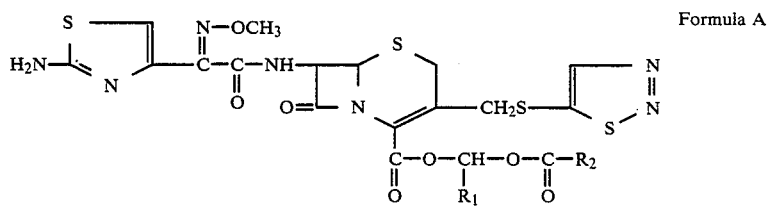

Formula A wherein $R_1$ is selected from the group consisting of hydrogen and $C_1$–$C_6$ alkyl and $R_2$ is selected from the group consisting of $C_1$–$C_6$ alkyl, aryl, (e.g., phenyl), adamantyl and —$OR_3$, where $R_3$ is selected from the group consisting of $C_1$–$C_6$ alkyl;

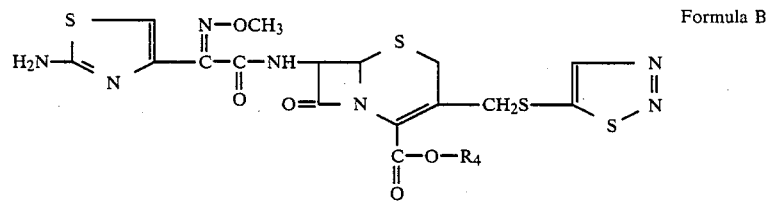

Formula B wherein $R_4$ is a cyclic system such as phthalidyl; and

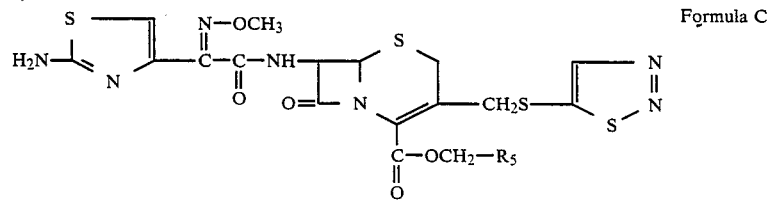

Formula C wherein $R_5$ is selected from the group consisting of methoxy, decyloxy, and methylthio.

Formula A compounds of the present invention may be prepared in accordance with the following Flowchart I.

tertiary amine, to produce the desired compound wherein $R_1$ and $R_2$ are as defined above. Alternatively the sodium salt of (i) may be employed in the process shown in Flowchart I.

As depicted in the following Flowchart II, use of the

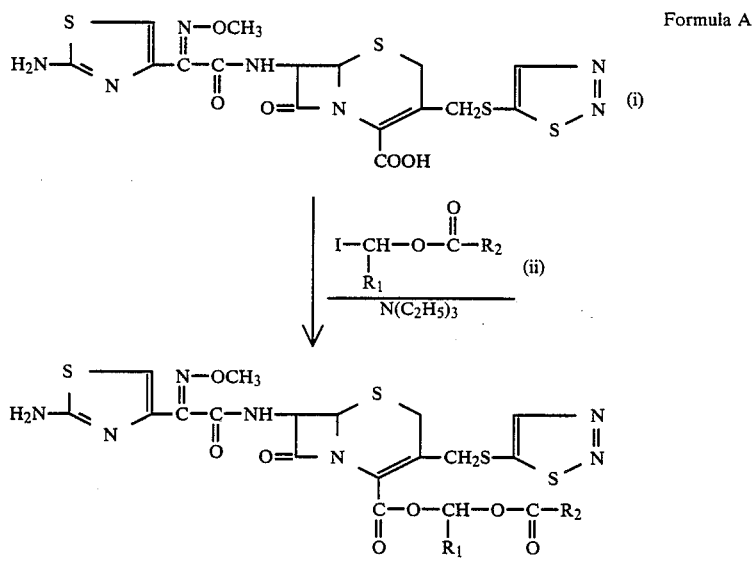

With regard to the above Flowchart I, the cephalosporin compound (i), 7β-[2-(2aminothiazol-4-yl)-(Z)-2-methoximinoacetamido]-3-[(1,2,3-thiadiazol-5-yl)-thiomethyl]ceph-3-em-4-carboxylic acid (described in Patent No. 4,399,132, which is incorporated herein by reference) is reacted with an appropriate alkylating agent (ii) in the presence of an acid acceptor, such as a bromo or chloro derivatives of alkylating agent (ii) may result in a mixture of $\Delta^2$ and $\Delta^3$ cephalosporins (iii) and (iv). Treatment of this mixture with m-chloroperbenzoic acid gives only the $\Delta^3$ sulfoxide (v) which is readily converted to the desired final product of Formula A by reaction with phosphorous trichloride, or other reducing agents.

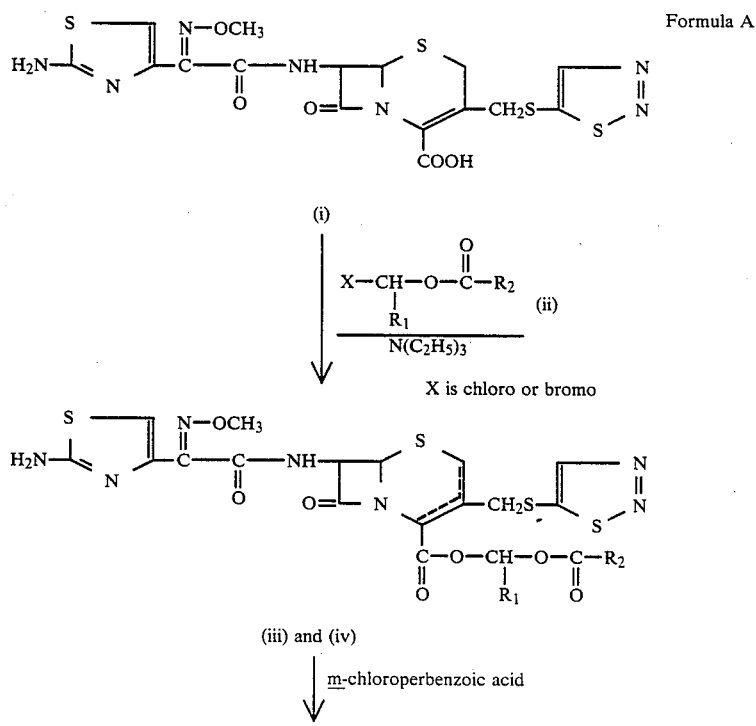

FLOWCHART II
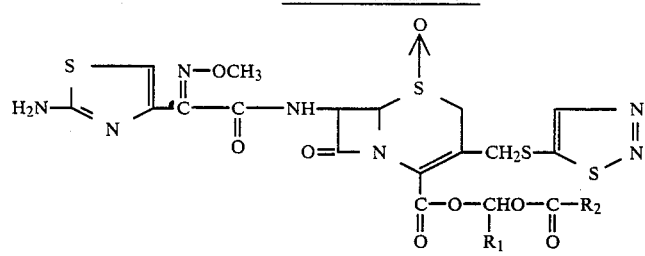
(v) ↓ phosphorous trichloride
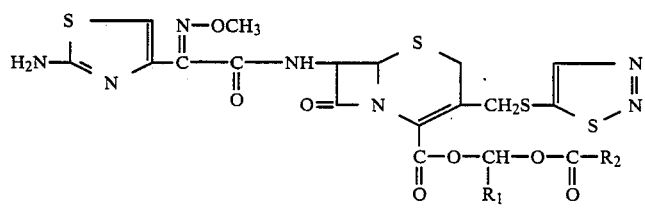
Formula A compounds of the present invention may also be prepared in accordance with the following Flowchart III.
FLOWCHART III
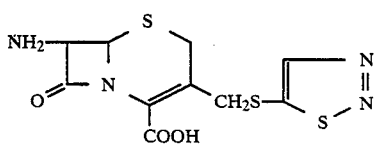
(iv) ↓ [(CH$_3$)$_3$C—OC]$_2$O
            ‖
            O
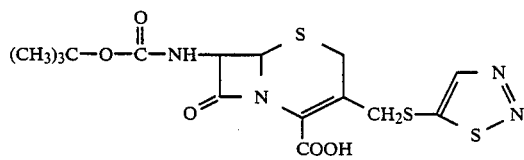
(vii) ↓ X—CH—O—C—R$_2$  (ii) X is Iodo,
         |        ‖        Fluoro or Bromo
         R$_1$    O
         ─────────────
         N(C$_2$H$_5$)$_3$
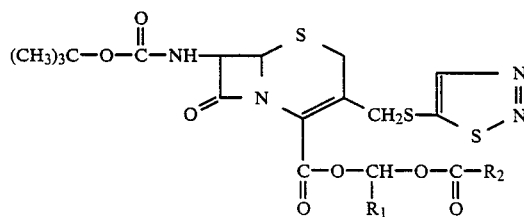
(viii) ↓ CF$_3$COOH
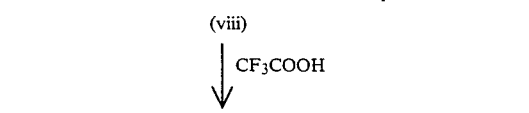

FLOWCHART III
-continued

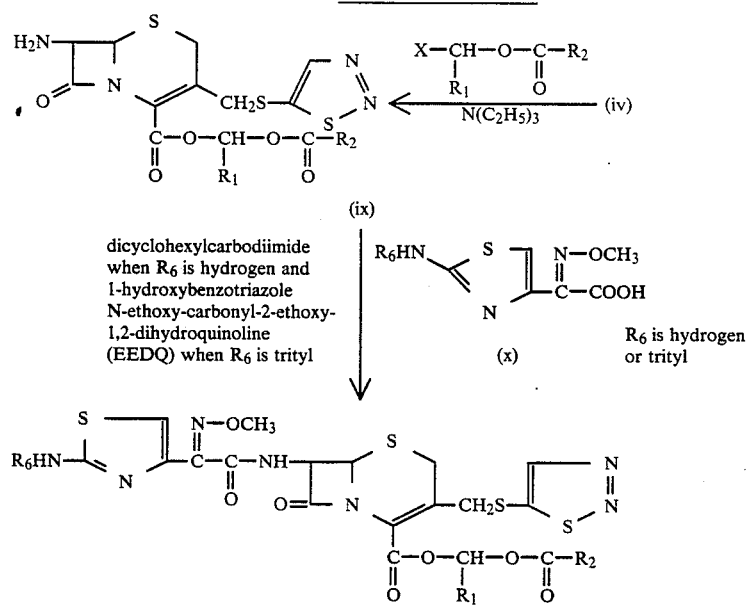

when $R_6$=trityl it must be removed using 80% formic acid.

With regard to the above Flowchart III, the amine group on the cephalosporin compound(vi) is optionally protected with any suitable protecting group, e.g., t-butyloxycarbonyl, through use of di-t-butyl dicarbonate from Aldrich Chemical Co., Milwaukee, Wis., to form cephalosporin compound (vii), which is then reacted with an appropriate alkylating agent (ii) in the presence of an acid acceptor, such as a tertiary amine, to produce cephalosporin compound (viii). The amine-protecting group if used, is then removed to produce cephalosporin compound (ix), which is then reacted with compound (x) in the presence of dicyclohexylcarbodiimide when $R_6$ is hydrogen and 1-hydroxybenzotriazole (or EEDQ when $R_6$ is trityl) to form cephalosporin of Formula A. Compound (ix) can also be synthesized directly from compound (vi) using the appropriate alkylating agent in the presence of an acid acceptor such as a tertiary amine.

The amine group on compound (x) may optionally be protected, e.g., with trityl, chloroacetyl or formyl, when reacted with cephalosporins compound (ix), in which case such protecting group would be removed to yield compounds of Formula A. Alternatively, the amino group of cephalosporin (vi) may also be protected, if desired, with a trityl or 2-methoxycarbonyl-1-methylvinyl group.

Compounds of Formula B and Formula C may be readily synthesized from the foregoing schemes of synthesis using modifications described in the examples provided herein below.

7β-[2-(2-aminothiazol-4-yl)-(Z)-2-methoximinoacetamido]-3-[(1,2,3-thiadiazol-5-yl)-thiomethyl]-ceph-3-em-4-carboxylic acid is a potent, third generation cephalosporin that is administered parenterally. By using the method of the present invention, such cephalosporin can be esterified to an orally-adminstratable pro-drug. As prodrugs, the compounds of the present invention exhibit significant oral in vivo activity in warm-blooded animals and the ratio of the subcutaneous/oral dose for most of the compounds is in the commercially acceptable range of about 4.0. Accordingly, in addition to providing a broad-spectrum oral cephalosporin that can be effectively utilized in the treatment of infections without hospitalization, the present invention also permits a patient to be treated for an infection both within and without the hospital with the same antibiotic. Oral formulations are also much preferred in pediatric use.

To establish the pro-drug activity of, for example, the pivaloyloxymethyl ester of 7β-[2-(2-aminothiazol-4-yl)-(Z)-2-methoximinoacetamido]-3-[(1,2,3-thiadiasol-5-yl)-thiomethyl]ceph-3-em-4-carboxylic acid, the unesterified carboxylic acid and cefaclor (as control) were administered by single subcutaneous dose and single oral dose to separate groups of Charles River CD-1 mice, each weighing about 20 g, which mice had been infected intraperitoneally with a lethal dose of Escherichia coli No. 311. The median effective doses ($ED_{50}$) in mg/kg were derived from the pooled data of three separate tests (including two range finding tests. The results of this testing appear in Table I.

TABLE I

| | In Vivo Activity of Cephalosporins Against Escherichia Coli No. 311 | | |
|---|---|---|---|
| | $ED_{50}$ (mg/kg) (95% Conf. Lim.) | | |
| Compound | Single Oral Dose | Single Subcut. Dose | Ratio Oral $ED_{50}$/ Subcutaneous $ED_{50}$ |
| Pivaloyloxy-methyl ester | 2 (1.5–2.7) | 0.53 (0.39–0.73) | 3.8 |
| Unesterified acid | 7.2 (5.0–11) | 0.26 (0.9–0.36) | 28 |
| Cefaclor | 16* | 5.7* | 2.8 |

*Cefaclor (control) - An orally active clinical agent. Estimated from two separate tests.

Other representative compounds of the present invention were similarly tested against a lethal infection of Klebsiella pneumoniae in mice. Charles River CD-1 mice, each weighing about 20 g, were infected intraperitoneally with a lethal dose of Klebsiella pneumoniae. The median effective doses ($ED_{50}$) in mg/kg were derived from the pooled data of three separate tests (including two range finding tests). The control, 7β-[2-(2-amino thiazol-4-yl)-(Z)-2-methoximinoacetamido]-3-[(1,2,3-thiadiazol-5-yl)-thiomethyl]ceph-3-em-4-carboxylic acid, provides a basis for comparison. All compounds were administered by single subcutaneous dose and single oral dose. The results of this test appear in Table II.

TABLE II

In Vivo Activity of Cephalosporins Against *Klebsiella Pneumoniae*

| Compound | $ED_{50}$ (mg/kg) (95% Conf. Lim.) Single Oral Dose | Single Subcut. Dose | Ratio Oral $ED_{50}$/Subcutaneous $ED_{50}$ |
|---|---|---|---|
| Control* | 8–16 | 0.5–1 | 16 |
| Acetoxyethyl ester | 2–4 | 1–2 | 2 |
| Phthalidyl ester | 8–16 | 0.5–1 | 16 |
| Ethoxycarbonyl-Ethoxyethyl ester | 1–2 | 0.5–1 | 2 |
| Adamantylcarbonyl-oxymethyl | 2–4 | 1–2 | 2 |
| Myristoyloxy-methyl ester | 8–16 | 0.5–1 | 16 |
| Methoxymethyl ester | 8–16 | 0.5–1 | 16 |
| Declyoxymethyl ester | 8–16 | 2–4 | 4 |
| Acetoxymethyl | 8–16 | 1–2 | 8 |
| methylthiomethyl ester | 8–16 | 2–4 | 4 |
| benzoyloxymethyl ester | 4–8 | 2–4 | 2 |

*7β-[2-(2-aminothiazol-4-yl)-(Z)-2-methoximinoacetamido]-3-[(1,2,3-thiadiazol-5-yl)-thiomethyl]ceph-3-em-4-carboxylic acid The active compounds of the present invention may be orally administered, for example, with an inert diluent or with an assimilable edible carrier, or they may be enclosed in hard or soft gelatin capsule shells, or they may be compressed into tablets, or they may be incorporated with food. For oral therapeutic administration, the active comounds may be incorporated with excipients and used in the form of tablets, troches, capsules, elixirs, suspensions, syrups, wafers and the life. Such compostions and preparations should contain at least about 0.1% of active compound. The percentage of the active compounds of the present invention in therapeutic preparations may, of course, be varied and may conveniently be between about 2% to about 60% of the weight of a preparation. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure, substantially non-toxic in the amounts employed and non-reactive with the esters of the present invention.

The invention will be described in greater detail in conjunction with the following specific examples.

EXAMPLE 1

Pivaloyloxymethyl 7β-[2-(2-aminothiazol-4-yl)-(Z)-2-methoximinoacetamido]-3-[(1,2,3-thiadiazol-5-yl)-thiomethyl]-ceph-3-em-4-carboxylate Method A A mixture of 513 mg of 7β-[2-(2-aminothiazol-4-yl)-(Z)-2-methoximinoacetamido]-3-[(1,2,3-thiadiazol-5-yl)-thiomethyl]ceph-3-em-4-carboxylic acid, 0.43 ml of chloromethyl pivalate and 0.50 g of potassium iodide in a mixture of about 5 ml of acetone and about 2 ml of dimethylformamide was stirred at room temperature (i.e., between about 15° C. to about 25° C.) for approximately 5 minutes. A solution of 0.14 ml of triethylamine in about 2 ml of acetone was added dropwise, over about one hour and the mixture was stirred for an additional approximate 0.5 hour. About 30 ml of ethyl acetate were added and this mixture was extracted successively with 1N-hydrochloric acid, water, saturated aqueous sodium bicarbonate and brine. The ethyl acetate solution was dried over magnesium sulfate and evaporated to a glass. This glass was purified by preparative thin layer chromatography on silica gel, using ethyl acetate to give the desired product as a beige solid, IR 1780 $cm^{-1}$ (β-lactam carbonyl).

Method B 443 mg of pivaloyloxymethyl 7β-[2-(2-aminothiazol-4-yl)-(Z)-2-methoximinoacetamido]-3-[(1,2,3-thiadiazol-5-yl)-thiomethyl]ceph-3-em-4-carboxylate-1-oxide and 0.24 ml of phosphorous trichloride were dissolved in about 80 ml of methylene chloride and stirred at room temperature for approximately 5 hours. This solution was extracted with about 100 ml of saturated aqueous sodium bicarbonate followed by about two 100 ml extractions with brine. The organic layer was dried over magnesium sulfate and evaporated to dryness. The residue was dissolved in about 25 ml of ethyl acetate and filtered through a pad of hydrous magnesium silicate. The filtrate was evaporated giving the desired product.

EXAMPLE 2

Pivaloylmethyl 7β-[2-(2-aminothiazol-4-yl)-(Z)-2-methoximinoacetamido]-3-[(1,2,3-thiadiazol-5-yl)-thiomethyl]-ceph-2-em-4-carboxylate and Pivaloyloxymethyl 7β-[2-(2-aminothiazol-4-yl)-(Z)-2-methoximinoacetamido]-3-[(1,2,3-thiadiazol-5-yl)-thiomethyl]-ceph-3-em-4-carboxylate A mixture of 0.52 ml of chloromethyl pivalate and 0.38 g of sodium bromide in approximately 2 ml of dimethylformamide was stirred at room temperature for approximately one hour and then filtered. The filtrate was added to a solution of about 0.95 g of 7β-[2-(2-aminothiazol-4-yl)-(Z)-2-methoximinoacetamido]-3-[(1,2,3-thiadiazol-5-yl)-thiomethyl]ceph-3-em-4-carboxylic acid and 0.26 ml of triethylamine in 25 ml of dimethylformamide. The reaction mixture was stirred at room temperature for approximately 4.5 hours, then about 100 ml of water was added and the mixture was extracted with approximately two 50 ml portions of ethyl acetate. The ethyl acetate extracts were combined, washed with saturated aqueous sodium bicarbonate, then water and finally brine and dried over magnesium sulfate. Evaporation of the solvent gave a glass which was triturated with ether, giving a solid. This layer chromatography and nuclear magnetic resonance showed that the product was a mixture of the $\Delta^2$ and $\Delta^3$ isomers, IR 1775 cm$^{-1}$ ($\beta$-lactam carbonyl).

EXAMPLE 3

Pivaloyloxymethyl-7$\beta$-[2-(2-aminothiazol-4-yl)-(Z)-2-methoximinoacetamido]-3-[(1,2,3-thiadiazol-5-yl)-thiomethyl]ceph-3-em-4-carboxylate-1-oxide A mixture of 612 mg of a mixture of the pivaloyloxymethyl esters of 7$\beta$-[2-(2-aminothiazol-4-yl)-(Z)-2-methoximinoacetamido]-3-[(1,2,3-thiadiazol-5-yl)-thiomethyl]ceph-2-em-4-carboxylate and 7-[2-(2-aminothiazol-4-yl)-(Z)-2-methoximinoacetamido]-3-[(1,2,3-thiadiazol-5-yl)-thiomethyl]ceph-3-em-4-carboxylate was dissolved in about 25 ml of chloroform and cooled in an ice bath. A solution of 245 mg of m-chloroperbenzoic acid in about 5 ml of chloroform was added and the mixture was stirred in the ice bath for several hours. About 50 ml of chloroform were added and the solution was extracted with approximately two 50 ml portions of saturated aqueous sodium bicarbonate, followed by about 50 ml of brine. The solution was dried over magnesium sulfate and evaporated to dryness. The residue was dissolved in a small amount of ethyl acetate and the desired product was precipitated by the addition of hexane, IR 1795 cm$^{-1}$ ($\beta$-lactam carbonyl).

EXAMPLE 4

Acetoxymethyl 7$\beta$-[2-(2-aminothiazol-4-yl)-(Z)-2-methoximinoacetamido]-3-[(1,2,3-thiadiazol-5-yl)thiomethyl]ceph-3-em-4-carboxylate Method A A mixture of 535 mg of 7$\beta$-[2-(2-aminiothiazol-4-yl)-(Z)-2-methoximinoacetamido]-3-[(1,2,3-thiadiazol-5-yl)-thiomethyl]ceph-3-em-4-carboxylic acid sodium salt and 0.20 ml of bromomethyl acetate in 5 ml of dimethyl formamide was stirred at room temperature for approximately 15 minutes. The reaction mixture was poured into about 100 ml of water and extracted with two approximately 50 ml portions of ethyl acetate. The combined ethyl acetate solution was extracted successively with saturated sodium bicarbonate solution, water and brine, then dried over magnesium sulfate. The ethyl acetate was evaporated and the the residue was triturated to a solid with ether and filtered to afford the desired ester, IR 1785 cm$^{-1}$ ($\beta$-lactam carbonyl).

Method B

Acetoxymethyl 7$\not\equiv$-[2-(2-tritylaminothiazol-4-yl)-(Z)-2-methoximinoacetamido]-3-[(1,2,3-thiadiazol-5-yl)-thiomethyl]ceph-3-em-4-carboxylate (1.0 g) was added to 10 ml of 80% aqueous formic acid and stirred at room temperature for 2 hours. Water (10 ml) was added and the mixture was filtered. The filtrate was evaporated to dryness at reduced pressure (bath temperature 40°) and the residue was slurried in 25 ml of ethyl acetate and 25 ml of saturated sodium bicarbonate solution. The ethyl acetate layer was separated and washed with water and brine then dried over magnesium sulfate. Evaporation of the ethyl acetate afforded the desired ester which was purified by chromatography on silica gel using ethyl acetate.

Method C 2-(2-aminothiazol-4-yl)-(Z)-2-methoximinoacetic acid (0.40 g), 0.305 g 1-hydroxybenzotriazole, and 0.410 g of dicyclohexylcarbodiimide in 10 ml of dimethylformamide was stirred at room temperature for 10 minutes. To this was added a solution of 0.80 g acetoxymethyl 7-amino-3-[(1,2,3-thiadiazol-5-yl)-thiomethyl]-ceph-3-em-4-carboxylate in 10 ml of dimethylformamide. The mixture was stirred at room temperature overnight then filtered. The filtrate was diluted with 75 ml of ethyl acetate and extracted successively with 75 ml portions of water, saturated sodium bicarbonate solution, water and brine. The ethyl acetate layer was dried over magnesium sulfate and evaporated to dryness at reduced pressure. The residue was slurried in ethyl acetate and filtered. The filtrate was evaporated to dryness and the product was purified by chromatography on silica gel using ethyl acetate.

EXAMPLE 5

Acetoxyethyl 7$\beta$-[2-(2-aminothiazol-4-yl)-(Z)-2-methoximinoacetamido]-3-[(1,2,3-thiadiazol-5-yl)-thiomethyl]-ceph-3-em-4-carboxylate A mixture of 535 mg of 7$\beta$-[2-(2-aminothiazol-4-yl)-(Z)-2-methoximinoacetamido]-3-[(1,2,3-thiadiazol-5-yl)-thiomethyl]ceph-3-em-4-carboxylic acid sodium salt and 0.2 ml of 1-bromoethyl acetate in approximately 5 ml of dimethylformamide was stirred at room temperature for about 3.5 hours. The reaction mixture was worked up as described in Example 4, Method A, to give the desired ester, IR 1785 cm$^{-1}$ ($\beta$-lactam carbonyl).

EXAMPLE 6

Ethoxycarbonyloxy-1-ethyl-7$\beta$-[2-(2-aminothiazol-4-yl)-(Z)-2-methoximinoacetamido[-3-[(1,2,3-thiadiazol-5-yl)thiomethyl]ceph-3-em-4-carboxylate A mixture of 534 mg of 7$\beta$-[2-(2-aminothiazol-4-yl)-(Z)-2-methoximinoacetamido]-3-[(1,2,3-thiadiazol-5-yl)-thiomethyl]ceph-3-em-4-carboxylic acid sodium salt and 0.5 ml of 1-iodoethyl-ethyl carbonate in about 5 ml of dimethylformamide was stirred at room temperature for approximately 30 minutes. The reaction mixture was treated as described in Example 4, Method A, to afford the desired ester, IR 1785 cm$^{-1}$ ($\beta$-lactam carbonyl).

EXAMPLE 7

Adamantane-1-carbonyloxymethyl-7$\beta$-[2-(2-aminothiazol-4-yl)-(Z)-2-methoximinoacetamido]-3-[(1,2,3-thiadiazol-5-yl)-thiomethyl]ceph-3-em-4-carboxylate A mixture of 504 mg of chloromethyl adamantane-1-carboxylate* and 33 mg of sodium iodide in about 7 ml of acetone was refluxed for approximately 0.5 hours, cooled to room temperature and filtered into a solution of 534 mg of 7$\beta$-[2-(2-aminothiazol-4-yl)-2-methoximinoacetamido]-3-[(1,2,3-thiadiazol-5-yl)-thiomethyl]-ceph-3-em-4-carboxylic acid sodium salt in about 5 ml of dimethylformamide. The reaction mixture was stirred at room temperature for approximately 0.5 hours and worked up as described in Example 4, Method A, to afford the desired compound, IR 1785 cm$^{-1}$ ($\beta$-lactam carbonyl).

*Prepared by the method described by L. H. Ulich and R. Adams, J. of Amer. Chem. Soc., 43, 660 (1921).

EXAMPLE 8

Benzoyloxymethyl 7β-[2-(2-aminothiazol-4-yl)-(Z)-2-methoxyiminoacetamido]-3-[(1,2,3-thiadiazol-5-yl)-thiomethyl]-ceph-3-em-4-carboxylate A mixture of 342 mg of chloromethyl benzoate and 300 mg of sodium iodide in about 7 ml of acetone was refluxed for approximately 0.5 hours, cooled to room temperature and filtered into a solution of 534 mg of 7β-[2-(2-aminothiazol-4-yl)-(Z)-2-methoxyiminoacetamido]-3-[(1,2,3thiadiazol-5-yl)-thiomethyl]-ceph-3-em-4-carboxylic acid sodium salt in about 5 ml of dimethylformamide. The reaction mixture was stirred at room temperature for approximately 0.5 hours. and worked up as described in Example 4, Method A, to give the desired compound, IR 1875 cm$^{-1}$ (β-lactam carbonyl).

EXAMPLE 9

Phthalidyl 7β-[2-(2-aminothiazol-4-yl)-(Z)-2-methoxyiminoacetamido]-3-[(1,2,3-thiadiazol-5-yl)-thiomethyl]-ceph-3-em-4-carboxylate A mixture of 213 mg of 3-bromophthalide and 150 mg of sodium iodide in about 5 ml of acetone was stirred for approximately 5 minutes then filtered into a solution of 534 mg of 7β-[2-(2-aminothiazol-4-yl)-(Z)-2-methoxyiminoacetamido]-3-[(1,2,3-thiadiazol-5-yl)-thiomethyl]-ceph-3-em-4-carboxylic acid sodium salt in about 5 ml of dimethylformamide. The reaction mixture was stirred at room temperature for approximately 5 minutes then worked up as described in Example 2 to give the desired ester; IR 1785 cm$^{-1}$ (β-lactam carbonyl).

EXAMPLE 10

Myristoyloxymethyl 7β-[2-(2-aminothiazol-4-yl)-(Z)-2-methoxyiminoacetamido]-3-[(1,2,3-thiadiazol-5-yl)-thiomethyl]-ceph-3-em-4-carboxylate To a mixture of 535 mg of 7β-[2-(2-aminothiazol-4-yl)-(Z)-2-methoxyiminoacetamido]-3-[(1,2,3-thiadiazol-5-yl)-thiomethyl]ceph-3-em-4-carboxylic acid sodium salt in about 5 ml of dimethylformamide was added a solution of iodomethyl myristate [prepared in situ by refluxing a solution of sodium iodide (300 mg) and chloromethyl myristate* (554 mg) in about 7 ml of acetone for approximately 0.5 hours]. The reaction mixture was stirred at room temperature for approximately 1.5 hours and then worked up as described in Example 2 to afford the desired compound. NMR indicated approximately 15% of the Δ$^2$ isomer was present.
*Prepared by the method of L. H. Ulich and Roger Adams, J. Am. Chem. Soc., 43, 660 (1921)

EXAMPLE 11

Methoxymethyl 7β-[2-(2-aminothiazol-4-yl)-(Z)-2-methoxyiminoacetamido]-3-[(1,2,3-thiadiazol-5-yl)-thiomethyl]-ceph-3-em-4-carboxylate A mixture of 535 mg of 7β-[2-(2-aminothiazol-4-yl)-(Z)-2-methoximinoacetamido]-3-[(1,2,3-thiadiazol-5-yl)-thiomethyl]ceph-3-em-4-carboxylic acid sodium salt and 0.15 ml of chloromethyl methylether in about 5 ml of dimethylformamide was stirred in the cold for approximately 5 minutes then worked up as Example 2 to give the desired compound, IR 1785 cm$^{-1}$ (β-lactam carbonyl).

EXAMPLE 12

Decyloxymethyl 7β-[2-(2-aminothiazol-4-yl)-(Z)-2-methoxyiminoacetamido]-3-[(1,2,3-thiadiazol-5-yl)-thiomethyl]-ceph-3-em-4-carboxylate A mixture of 535 mg of 7β-[2-(2-aminothiazol-4-yl)-(Z)-2-methoximinoacetamido]-3-[(1,2,3-thiadiazol-5-yl)-thiomethyl]ceph-3-em-4-carboxylic acid, sodium salt and 0.3 ml of chloromethyl dodecyl ether in about 5 ml of dimethylformamide was stirred in the cold for approximately 5 minutes then worked up as described in Example 2 to afford the desired product, IR 1785 cm$^{-1}$ (β-lactam carbonyl).

EXAMPLE 13

Methylthiomethyl 7β-[2-(2-aminothiazol-4-yl)-(Z)-2-methoxyiminoacetamido]-3-[(1,2,3-thiadiazol-5-yl)-thiomethyl]-ceph-3-em and ceph-2-em-carboxylate A mixture of 534 mg of 7β-[2-(2-aminothiazol-4-yl)-(Z)-2-methoximinoacetamido]-3-[(1,2,3-thiadiazol-5-yl)-thiomethyl]ceph-3-em-4-carboxylic acid sodium salt and 0.2 ml of chloromethyl methyl sulfide in about 5 ml of dimethylformamide was stirred at room temperature for approximately 2 hours then worked up as described in Example 2 to afford a mixture of about 60% of the Δ$^3$ and about 40% of Δ$^2$ isomers as indicated by NMR.

EXAMPLE 14

7-[(t-butyloxycarbonyl)amino]-3-[(1,2,3-thiadiazol-5-yl)-thiomethyl]-ceph-3-em-4-carboxylic acid A solution of di-t-butyl dicarbonate (3.20 ml) in 40 ml. of dioxane was added to a solution of 7-amino-3-[1,2,3-thiadiazol-5-yl]thiomethyl]-ceph-3-em-carboxylic acid (4.0 g) and sodium bicarbonate (2.04 g) in 50 ml of water. The mixture was stirred at room temperature overnight then cooled in an ice bath and acidifided to pH2 with 4N hydrochloric acid The resulting precipitate was collected and dried then extracted with ethyl acetate. The ethyl acetate was evaporated at reduced pressure and the residue was triturated with hexane to afford the desired product, IR 1780 cm$^{-1}$ (β-lactam carbonyl).

EXAMPLE 15

Acetoxymethyl 7-[(t-butyloxycarbonyl)amino]-3-[(1,2,3-thiadiazol-5-yl)-thiomethyl]-ceph-3-em-4-carboxylate Bromomethyl acetate (0.10 ml) was added to a solution of 418 mg of 7-[(t-butyloxycarbonyl)amino]-3-[1,2,3-thiadiazol-5-yl)-thiomethyl]-ceph-3-em carboxylic acid and 0.17 ml of di-isopropylethylamine in 5 ml of dimethylformamide. The mixture was stirred at room temperature for 10 minutes then worked up as described in Example 4, Method A, to give the desired compound, IR 1780 cm$^{-1}$ (β-lactam carbonyl).

EXAMPLE 16

Acetoxymethyl 7-amino-3-[(1,2,3-thiadiazol-5-yl)-thiomethyl]-ceph-3-em-4-carboxylate Method A Acetoxymethyl 7-[(t-butyloxycarbonyl)amino]-3-[(1,2,3-thiadiazol-5-yl)-thiomethyl]ceph-3-em-4-carboxylate (350 mg) was added to 4 ml of trifluoroacetic acid then evaporated at reduced pressure (40°). The residue was slurried with 25 ml of ethyl acetate and 25 ml of saturated sodium bicarbonate solution. The ethyl acetate phase was separated and washed with water and brine, then dried over magnesium sulfate. Evaporation of the ethyl acetate afforded the title compound, IR 1780 cm$^{-1}$ ($\beta$-lactam carbonyl).

Method B

Bromomethyl acetate (1.0 ml) was added to a solution of 3.30 g 7-amino-3-[(1,2,3-thiadiazol-5-yl)-thiomethyl]-ceph-3-em-4-carboxylic acid and 1.4 ml of triethylamine in 40 ml of dimethylformamide. The mixture was stirred at room temperature for 15 minutes then worked up as described in Example 4 to give the amino ester.

EXAMPLE 17

Acetoxymethyl 7$\beta$-[2-(2-tritylaminothiazol-4-yl)-(Z)-2-methoximinoacetamido]-3-[(1,2,3-thiadiazol-5-yl)thiomethyl]-ceph-3-em-4-carboxylate A mixture of 1.07 g 2-(2-tritylaminothiazol-4-yl)-(Z)-2-methoximinoacetic acid, 0.975 g of acetoxymethyl 7-amino-3-[(1,2,3-thiadiazol-5-yl)-thiomethyl]-ceph-3-em-4-carboxylate, and 0.60 g of ethyl 1,2-dihydro-2-ethoxy-1-quinolinecarboxylate in 40 ml of methylene chloride was stirred at room temperature overnight. The solvent was evaporated to near dryness at reduced pressure and replaced with ethyl acetate. The ethyl acetate solution was washed successively with 75 ml aliquots of 0.5N hydrochloric acid, water, saturated sodium bicarbonate solution, water and brine then dried over magnesium sulfate. The ethyl acetate was evaporated at reduced pressure and the resulting product was purified by chromatograhy on silica gel using ethyl acetate:hexane (1:1), IR 1785 cm$^{-1}$ ($\beta$-lactam carbonyl).

What is claimed is:

1. The compound adamantane-1-carbonyloxymethyl 7$\beta$-[2-(2-aminothiazol-4-yl)-(Z)-2-methoximinoacetamido]-3-[(1,2,3-thiadiazol-5-yl)-thiomethyl]-ceph-3-em-4-carboxylate.

2. The method for treating bacterial infections in warm blooded animals which comprises orally administering to said animals an effective amount of the compound adamantane-1-carbonyloxymethyl 7$\beta$-[2-(2-aminothiazol-4-yl)-(Z)-2-methoximinoacetamido]-3-[(1,2,3-thiadiazol-5-yl)-thiomethyl]ceph-3-em-4-carboxylate.

3. The composition of matter which comprises an effective amount of the compound adamantane-1-carbonyloxymethyl 7$\beta$-[2-(2-aminothiazol-4-yl)-(Z)-2-methoximinoacetamido]-3-[(1,2,3-thiadiazol-5-yl)-thiomethyl]ceph-3-em-4-carboxylate in association with a pharmaceutically effective carrier.

* * * * *